United States Patent [19]

Wilcox

[11] Patent Number: 4,683,869
[45] Date of Patent: Aug. 4, 1987

[54] BREATH TRANSFER DEVICE

[76] Inventor: Robert B. Wilcox, 401 W. Lexington Ave., El Cajon, Calif. 92020

[21] Appl. No.: 860,376

[22] Filed: May 6, 1986

[51] Int. Cl.$^4$ .............................................. A61F 7/00
[52] U.S. Cl. .............................. 126/204; 128/204.17; 128/201.13
[58] Field of Search ................... 126/204; 128/204.17, 128/201.13

[56] References Cited

U.S. PATENT DOCUMENTS

| | | | |
|---|---|---|---|
| 1,731,700 | 10/1929 | Battenfeld . | |
| 2,551,142 | 5/1951 | Lessard | 126/204 |
| 2,707,966 | 5/1955 | Nebel | 128/204.17 |
| 3,153,720 | 10/1964 | Petronio et al. | 126/204 |
| 3,229,681 | 1/1966 | Gluckstein | 126/204 |
| 3,345,641 | 10/1967 | Jennings | 2/2.1 |
| 4,038,698 | 8/1977 | Smith | 126/204 |
| 4,441,494 | 4/1984 | Montalbano | 128/204.17 |
| 4,492,228 | 1/1985 | Makovic | 128/204.17 |

Primary Examiner—Samuel Scott
Assistant Examiner—H. A. Odar
Attorney, Agent, or Firm—Richard J. Donahue; Donald J. Singer

[57] ABSTRACT

A breath transfer device which uses the heat of exhaled air to warm the body of the wearer of the device in cold environments, and which facilitates condensation of moisture in the device to eliminate the formation of vapor clouds. The device uses a mouthpiece into which exhaled air is blown, and a length of insulated tubing to direct the warm air to a vest-like radiating chamber garment. The moisture in the expelled air condenses on the inner surfaces of the chamber and is retained in special condensing pockets formed at the ends of internal partitions which provide a sinuous path for air flow through the chamber. Cooled dry air is finally exhausted at the lowermost point of the radiating chamber.

5 Claims, 6 Drawing Figures

BREATH TRANSFER DEVICE

STATEMENT OF GOVERNMENT INTEREST

The invention described herein may be manufactured and used by or for the government for governmental purposes without the payment of any royalty thereon.

BACKGROUND OF THE INVENTION

This invention concerns a device for reducing body heat loss and concomitantly diminishing the possibility of detection of the user thereof in cold weather environments.

Various suits and related garments have been developed whose insulative properties retain body heat and permit the wearers thereof to endure in the cold environments often experienced by hunters and military combat troops. While such suits achieve some degree of success for short exposure times, the insulation required for long exposure times becomes relatively thick, resulting in a heavy, bulky suit in which it becomes difficult to function.

Cold weather suits having battery powered heating elements are also well known. The limited life, expense and weight of such batteries, however, as well as the reduced efficiency thereof at very low temperatures are serious drawbacks to their use in battlefield conditions.

An additional problem encountered by hunters and military combat personnel is the possibility of their being detected in cold weather due to the so-called "white flagging effect", i.e. the formation of vapor clouds due to moisture in their exhaled breath.

OBJECTS AND SUMMARY OF THE INVENTION

It is therefore an object of the present invention to provide a breath transfer device for reducing body heat loss and concomitantly preventing the formation of vapor clouds formed by exhaled breath.

It is a further object of the present invention to provide a breath transfer device of improved performance and reduced cost.

It is yet another object of the present invention to provide a breath transfer device which is easy to manufacture and of small physical size and low weight.

It is yet another object of the present invention to provide a body heating device which does not require the use of batteries or chemical substances.

The invention disclosed herein which achieves the aforementioned objectives basically comprises a mouthpiece or mask into which exhaled air is blown by the user, and a length of insulating tubing which directs the warm exhaled air to a radiating chamber garment affixed to the user. Moisture in the expelled air condenses in the chamber and is retained in pockets formed therein. A pair of check valves may be included in the intake and exhaust air streams to provide a one-way flow of air from the environment into the mouthpiece and thence to the user, and from the user into the mouthpiece and thence to the radiating chamber.

BRIEF DESCRIPTION OF THE DRAWINGS

Additional objectives, features and advantages of the present invention will be apparent from the following description when read in conjunction with the accompanying drawings wherein.

DESCRIPTION OF THE PREFERRED EMBODIMENT

Figure 1:
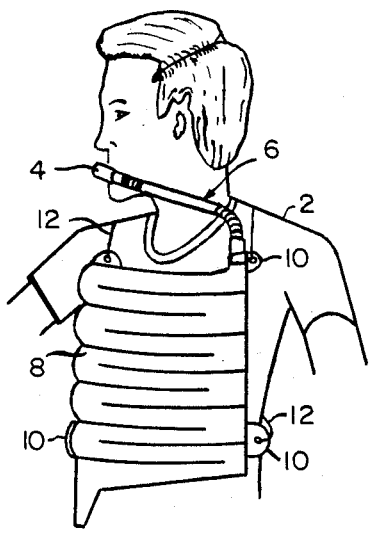
FIG. 1 is a pictorial drawing of the present invention as affixed to a user thereof.

Referring now specifically to FIG. 1 of the drawings, there is shown the preferred embodiment of the breath tranfer device of the present invention as it is attached to the chest of a person 2. The device includes a mouthpiece 4, a length of insulated tubing 6, and a vest-like radiating chamber 8. Chamber 8 is of generally rectangular shape and has body strap tabs 10 affixed thereto for attachment of chamber 8 to the user 2 by means of string members 12.

It will be appreciated that radiating chamber 8 may be differently shaped and dimensioned to cover other parts of the user. For example, chamber 8 could be shaped to cover the back, as well as, or instead of the chest of the user.

Figure 2:
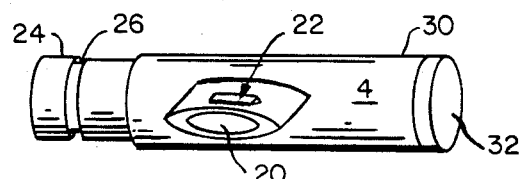
FIG. 2 is a pictorial drawing of the mouthpiece of the present invention.

FIG. 2 illustrates mouthpiece 4 in greater detail. It will be seen to be of generally cylindrical shape and has a breath flow port 20 with a tooth process member 22 affixed to the outer wall thereof. End 24 of the mouthpiece 4 is open to form an expelled air port and is reduced slightly in diameter to fit within the insulated tube 6. It also has a groove 26 therein for retaining the mouthpiece 4 in tube 6 via an elastic string (not shown) which encircles the exterior of tube 6. The other end 30 of mouthpiece 4 may either be closed by way of a cap 32 or may be open to receive one of a pair of check valves 40, of conventional design.

Figure 3:
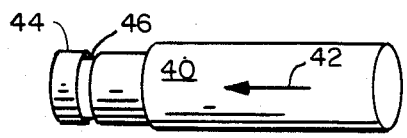
FIG. 3 is a pictorial drawing of a flow check valve of the present invention.

A pictorial representation of the exterior of a conventional air flow check valve 40, which permits air flow only in the direction shown by the arrow 42, is shown in FIG. 3 of the drawings. The end 44 of check valve 40 is also reduced in diameter to be accommodated within the end 30 of mouthpiece 4, and has a string groove 46. A second check valve identical to the check valve 40 of FIG. 3 may be included between the end 24 of mouthpiece 40 and tube 6.

It will be appreciated that mouthpiece 4 may take other forms, and includes devices which are either inserted into the mouth, as depicted herein, or to which the mouth is applied. In another embodiment, for example, the mouthpiece may take the form of a breath confining mask which covers both the mouth and nose of the user, and having an external air port and an expelled air port with air check valves associated therewith.

Figure 4:
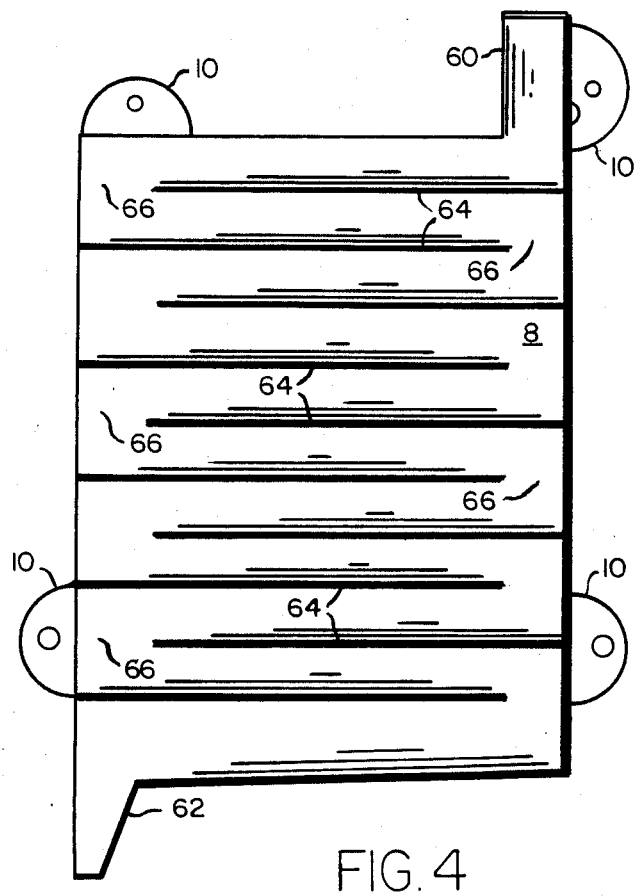
FIG. 4 is a pictorial drawing of the vest-like radiating chamber of the present invention.

FIG. 4 illustrates the radiating chamber 8 in somewhat greater detail. It will be seen to have an air input port 60, to which tube 6 is attached, and an exhaust port 62. Chamber 8 is preferably made of inflatable plastic material which is sufficiently flexible to be folded and stored in a small packet. The outlines of internal partitions or walls 64 are visible in this pictorial view. Partitions 64 are preferably formed by bonding together the front and back surfaces of chamber 8 at a series of horizontal and parallel strips. Alternatively, partitions 64 may be separate internal walls having a height which extends between the front and back surfaces of chamber 8. In either case, adjacent ones of the partitions 64 abut opposite side surfaces of chamber 8 and have a gap or space 66 between the free end thereof and the other sidewall to form a sinuous path for air flow through chamber 8.

Figure 5:
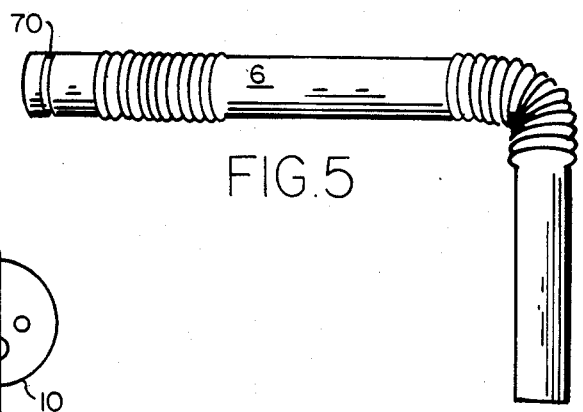
FIG. 5 is a pictorial drawing of the insulated tubing of the present invention.

FIG. 5 illustrates tube 6 in greater detail. It will be seen to also have a string groove 70 and is preferably formed of insulative material or has an insulative material covering the outer surface thereof.

In operation, air is blown into the mouthpiece 4 and immediately flows through check valve 40 disposed between the mouthpiece 4 and the tube 6. It then flows through tube 6 into chamber 8. During inhalation, the check valve 40 closes to prevent reverse air flow from chamber 8 and tube 6 into the mouthpiece 4. At this time, a second check valve 40 located in the port formed in end 30 of mouthpiece 4 opens to permit the entry of outside air into mouthpiece 4. This check valve is not necessarily needed in instances where air is inhaled through the nasal passage of the user and exhaled through the mouth into mouthpiece 4.

As warm air (98F/36C) travels through the radiating chamber 8 it gradually loses heat which is absorbed into the clothing of the wearer. Moisture in the expelled air condenses onto the inner partition or walls 64 of radiating chamber 8.

Figure 6:
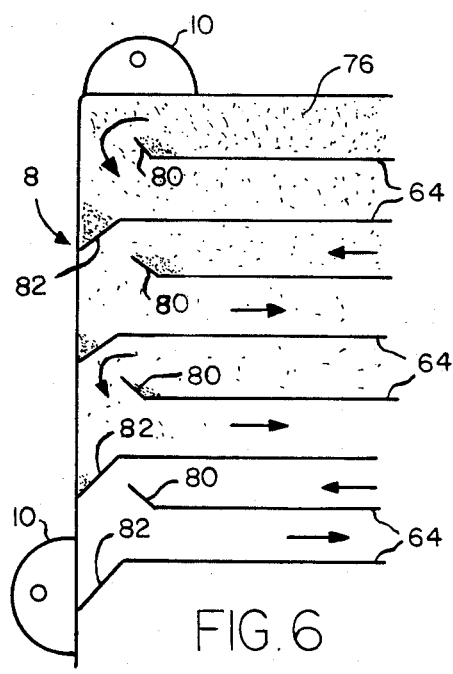
FIG. 6 is a cross-sectional view of a portion of the radiating chamber of the present invention.

FIG. 6 is a cross-sectional view of the upper left hand portion of the radiating chamber 8. The stippling 76 is intended to illustrate moisture in the air of which enters the chamber 8 and flows in the direction of the arrows in this figure. It will be seen that the moisture 76 is condensed as the air travels in a sinuous path towards the bottom of chamber 8. The condensed moisture 76 is prevented from flowing downwardly in chamber 8 by the action of the baffles 80 formed at the free end of each of the partitions 64 and is retained in pockets 82 formed at the juncture of partitions 64 with the sidewalls of chamber 8. The cooler and dryer air finally emerges from the bottom of chamber 8.

Although the preferred embodiment of the invention is described in detail above, it is to be understood that various changes, substitutions and alterations can be made therein without departing from the spirit and scope of the invention as defined by the appended claims.

What is claimed is:

1. Apparatus for reducing body heat loss and concomitantly preventing the formation of vapor clouds formed by exhaled breath in a cold weather environment comprising:
   a heat radiating chamber having a top, a bottom, a front, a back, opposed sides, an air input port and an exhaust port;
   said air input port being located near the top of said chamber;
   said exhaust port being located near the bottom of said chamber;
   said chamber having a plurality of internal partitions being disposed in parallel across the width of said chamber, adjacent ones of said partitions abutting and extending from opposite sides of said chamber part way across the width of said chamber to provide gaps for completing a sinuous air flow path through said chamber;
   means affixed to said chamber for securing said chamber against a portion of the body of a user;
   breath confining means having an expelled air port; and
   a tube for coupling said expelled air port of said breath confining means to said air input port of said chamber.

2. Apparatus as defined in claim 1 wherein said breath confining means comprises a mouthpiece having:
   a breath flow port;
   an external air input port having a first check valve therein permitting only a one-way flow of air from said environment into said mouthpiece; and
   a second check valve inserted between said expelled air port of said mouthpiece and said tube permitting only a one-way flow of air from said mouthpiece into said chamber.

3. Apparatus as defined in claim 2 wherein said tube is an insulated tube and wherein each of said plurality of internal partitions has a moisture catching pocket formed at the juncture thereof with a side of said chamber and an upwardly projecting moisture retaining baffle formed at the end thereof removed from a side of said chamber.

4. Apparatus as defined in claim 3 wherein said chamber is made of inflatable plastic material.

5. Apparatus as defined in claim 4 wherein said gaps have a dimension substantially equal to the spacing between adjacent ones of said plurality of partitions.

* * * * *